(12) United States Patent
Goddard et al.

(10) Patent No.: US 10,888,313 B2
(45) Date of Patent: Jan. 12, 2021

(54) REUSABLE IMPLANT DELIVERY DEVICES

(71) Applicant: Boston Scientific Scimed, Inc., Maple Grove, MN (US)

(72) Inventors: James M. Goddard, Pepperell, MA (US); Kenneth W. Adams, Maynard, MA (US); Doreen Rao, Sudbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 394 days.

(21) Appl. No.: 15/219,822

(22) Filed: Jul. 26, 2016

(65) Prior Publication Data

US 2017/0027659 A1 Feb. 2, 2017

Related U.S. Application Data (60) Provisional application No. 62/199,647, filed on Jul. 31, 2015.

(51) Int. Cl.
*A61B 17/06* (2006.01)
*A61F 2/00* (2006.01)
*A61B 90/00* (2016.01)
*A61B 17/00* (2006.01)

(52) U.S. Cl.
CPC ........ *A61B 17/06* (2013.01); *A61B 17/06109* (2013.01); *A61F 2/0063* (2013.01); *A61B 90/08* (2016.02); *A61B 2017/0042* (2013.01); *A61B 2017/00433* (2013.01);
(Continued)

(58) Field of Classification Search
CPC ... A61B 90/08; A61B 17/06109; A61B 17/06; A61B 2017/00486; A61B 2017/00433; A61B 2017/0042; A61B 2090/0813; A61B 17/3401; A61B 17/34; A61F 2/0063; A61F 2002/0072
See application file for complete search history.

(56) References Cited

U.S. PATENT DOCUMENTS

| | | | | |
|---|---|---|---|---|
| 5,054,154 A | * | 10/1991 | Schiffer | A46B 5/0062 15/167.1 |
| 6,419,658 B1 | * | 7/2002 | Restelli | A61M 5/326 604/110 |
| 9,533,120 B1 | * | 1/2017 | Kimmel | A61M 25/0102 |

(Continued)

FOREIGN PATENT DOCUMENTS

| | | |
|---|---|---|
| AU | 2013252558 A1 | 9/2014 |
| CN | 1161640 A | 10/1997 |

(Continued)

OTHER PUBLICATIONS

International Search Report and Written Opinion for PCT Application No. PCT/US2016/44191, dated Dec. 14, 2016, 19 pages.

(Continued)

*Primary Examiner* — Amy R Weisberg
(74) *Attorney, Agent, or Firm* — Brake Hughes Bellermann LLP (57) ABSTRACT

According to an aspect, a medical device includes a needle member and a handle member. The handle member is coupled to the needle member. The handle member has a substantially flat portion. The handle member defines a groove. The groove is disposed on the substantially flat portion of the handle member.

18 Claims, 8 Drawing Sheets

(52) U.S. Cl.
CPC .............. *A61B 2017/00486* (2013.01); *A61B 2090/0813* (2016.02); *A61F 2002/0072* (2013.01)

(56) References Cited

U.S. PATENT DOCUMENTS

| | | | |
|---|---|---|---|
| 2003/0065246 A1 | 4/2003 | Inman et al. | |
| 2004/0087970 A1* | 5/2004 | Chu | A61B 17/00234 606/119 |
| 2004/0097975 A1* | 5/2004 | Rose | A61B 17/0401 606/145 |
| 2004/0116962 A1* | 6/2004 | Batke | A61B 17/06109 606/222 |
| 2004/0144395 A1* | 7/2004 | Evans | A61B 17/06066 128/885 |
| 2005/0131391 A1* | 6/2005 | Chu | A61B 17/00234 606/1 |
| 2005/0131392 A1* | 6/2005 | Chu | A61B 17/00234 606/1 |
| 2005/0131393 A1* | 6/2005 | Chu | A61B 17/00234 606/1 |
| 2008/0132753 A1* | 6/2008 | Goddard | A61B 17/06109 600/37 |
| 2008/0139877 A1* | 6/2008 | Chu | A61B 17/0469 600/30 |
| 2008/0287731 A1 | 11/2008 | Kuntz | |
| 2009/0082788 A1* | 3/2009 | ElMaraghy | A61B 17/0483 606/148 |
| 2009/0158540 A1* | 6/2009 | Baertschi | A46B 5/0025 15/143.1 |
| 2010/0256611 A1* | 10/2010 | Hansen | A61B 17/0057 606/1 |
| 2011/0257581 A1 | 10/2011 | Koziczynski et al. | |
| 2012/0059403 A1* | 3/2012 | Domingues | A61B 17/02 606/190 |
| 2014/0059792 A1* | 3/2014 | Naccour | A46B 9/023 15/160 |
| 2014/0378757 A1* | 12/2014 | Allen | A61F 2/0045 600/37 |
| 2016/0038179 A1* | 2/2016 | Rao | A61B 17/00234 600/37 |
| 2016/0074147 A1* | 3/2016 | Pereira | A61B 17/3417 600/37 |

FOREIGN PATENT DOCUMENTS

| | | |
|---|---|---|
| EP | 1531737 B1 | 12/2008 |
| EP | 2191777 A1 | 6/2010 |
| GB | 2353220 A | 2/2001 |
| JP | 08206128 A | 8/1996 |
| JP | 2006502800 A | 1/2006 |
| JP | 2006517115 A | 7/2006 |
| JP | 2008528205 A | 7/2008 |
| WO | 0193656 A2 | 12/2001 |
| WO | 2004016196 A2 | 2/2004 |
| WO | 2006081545 A1 | 8/2006 |
| WO | 2012083159 A2 | 6/2012 |
| WO | 2013123036 A2 | 8/2013 |

OTHER PUBLICATIONS

Invitation to Pay Add'l Fees and Partial Search Rpt for PCT Application No. PCT/US2016/44191, dated Oct. 17, 2016, 9 Pages.
Communication pursuant to Article 94(3) EPC for European Application No. 16753507.9, dated Dec. 21, 2018, 6 pages.
Office Action for Japanese Application No. 2018-504726 (with English Translation), dated Nov. 19, 2018, 5 pages.
Third Office Action for Chinese Application No. 201680028463.6 (with English Translation), dated Oct. 12, 2020, 17 pages.

* cited by examiner

REUSABLE IMPLANT DELIVERY DEVICES

CROSS REFERENCE TO RELATED APPLICATION

This application is a Nonprovisional of, and claims priority to, U.S. Patent Application No. 62/199,647, filed on Jul. 31, 2015, entitled "REUSABLE IMPLANT DELIVERY DEVICES", which is incorporated by reference herein in its entirety.

TECHNICAL FIELD

This disclosure relates generally to medical devices, surgical procedures, and techniques for using medical devices, and particularly reusable medical devices for delivering implants, and methods of using such reusable medical devices.

BACKGROUND

Most conventional sling delivery devices are designed for single-use. For example, after a delivery device is used within a surgical procedure for implanting a sling, the single-use sling delivery device is discarded. For example, during the surgical procedure, bodily fluids or other contaminating substances may be embedded within components or between components of the delivery device, which may be relatively difficult to clean and sterilize. Additionally, some conventional sling delivery devices may require that the delivery device be disassembled (or the components of the delivery device be separated) to sterilize the delivery device and then re-assembled to be used in a subsequent surgical procedure.

Accordingly, there may be a need for a medical device, such as a delivery tool or delivery device, that allows for reuse of the device and does not require the disassembly of the medical device. Additionally, there may be a need for a medical device, such as a delivery device, that includes features or portions that help facilitate the use of the device.

SUMMARY

According to an aspect, a medical device includes a needle member and a handle member. The handle member is coupled to the needle member. The handle member has a substantially flat portion. The handle member defines a groove. The groove is disposed on the substantially flat portion of the handle member.

In some aspects, the handle member defines a longitudinal axis and the groove extends in a direction substantially perpendicular to the longitudinal axis of the handle member. In some aspects, the handle member has a rounded portion, the rounded portion is disposed on a top side of the handle member, the substantially flat portion is disposed on a bottom side of the handle member, the top side of the handle member is opposite the bottom side of the handle member.

In some aspects, the needle member includes a curved portion. In some aspects, the needle member includes a substantially linear portion and a curved portion. In some aspects, the needle member includes a first portion having a first diameter and a second portion having a second diameter, the second diameter is larger than a first diameter. In some aspects, the needle member defines a ridge configured to contact a portion of a bodily implant.

In some aspects, the handle member is coupled to the needle member via an adhesive, such as an epoxy or epoxy material. In some aspects, the handle member defines a cavity, at least a portion of the needle member is disposed within the cavity. In some aspects, the handle member defines a cavity having an inner surface, at least a portion of the needle member is disposed within the cavity, the needle portion having a projection, the projection is configured to be disposed within the cavity and being configured to engage the inner surface of the cavity of the handle member.

In some aspects, the needle member is formed of a metal material. In some aspects, the handle member is formed of a plastic-based material. In some aspects, the medical device is configured to be cleaned after use.

In some aspects, a medical device includes a needle member and a handle member. The needle member defines a projection. The handle member is coupled to the needle member. The handle member defines a cavity having an inner surface. The handle member is coupled to the needle member such that the projection defined by the needle member is disposed within the cavity and engages the inner surface of the cavity.

In some aspects, the needle member includes a curved portion. In some aspects, the needle member includes a substantially linear portion and a curved portion. In some aspects, the needle member includes a first portion having a first diameter and a second portion having a second diameter, the second diameter being larger than a first diameter. In some aspects, the needle member defines a ridge configured to contact a portion of a bodily implant. In some aspects, the handle member is coupled to the needle member via an adhesive.

In some aspects, a method includes using a device for a first medical procedure, the medical device having a needle member, and a handle member coupled to the needle member, the handle member having a substantially flat portion, the handle member defining a groove, the groove being disposed on the substantially flat portion; cleaning the device; and using the medical device for a second medical procedure.

In some aspects, the using the device for the first medical procedure includes placing a bodily implant within a body of a patient. In some aspects, the handle member of the device defines a longitudinal axis, the groove extends in a direction substantially perpendicular to the longitudinal axis of the handle member. In some aspects, the handle member of the device has a rounded portion, the rounded portion being disposed on a top side of the handle member, the substantially flat portion being disposed on a bottom side of the handle member, the top side of the handle member being opposite the bottom side of the handle member.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition).

The term patient may hereafter be used for a person who benefits from the medical device or the methods disclosed in the present application. For example, the patient can be a person whose body is operated through the medical device or the method disclosed by the present invention. For example, in some aspects, the patient may be a human female, a human male, or any other mammal.

The terms proximal and distal described in relation to various devices, apparatuses, and components as discussed in the subsequent text of the present application are referred with a point of reference. The point of reference, as used in this description, is a perspective of an operator. The operator may be a surgeon, a physician, a nurse, a doctor, a technician, and the like who may perform the procedure and operate the medical device as described in the present invention. The term proximal refers to an area or portion that is closer or closest to the operator during a surgical procedure. The term distal refers to an area or portion that is farther or farthest from the operator.

Figures 1, 2:
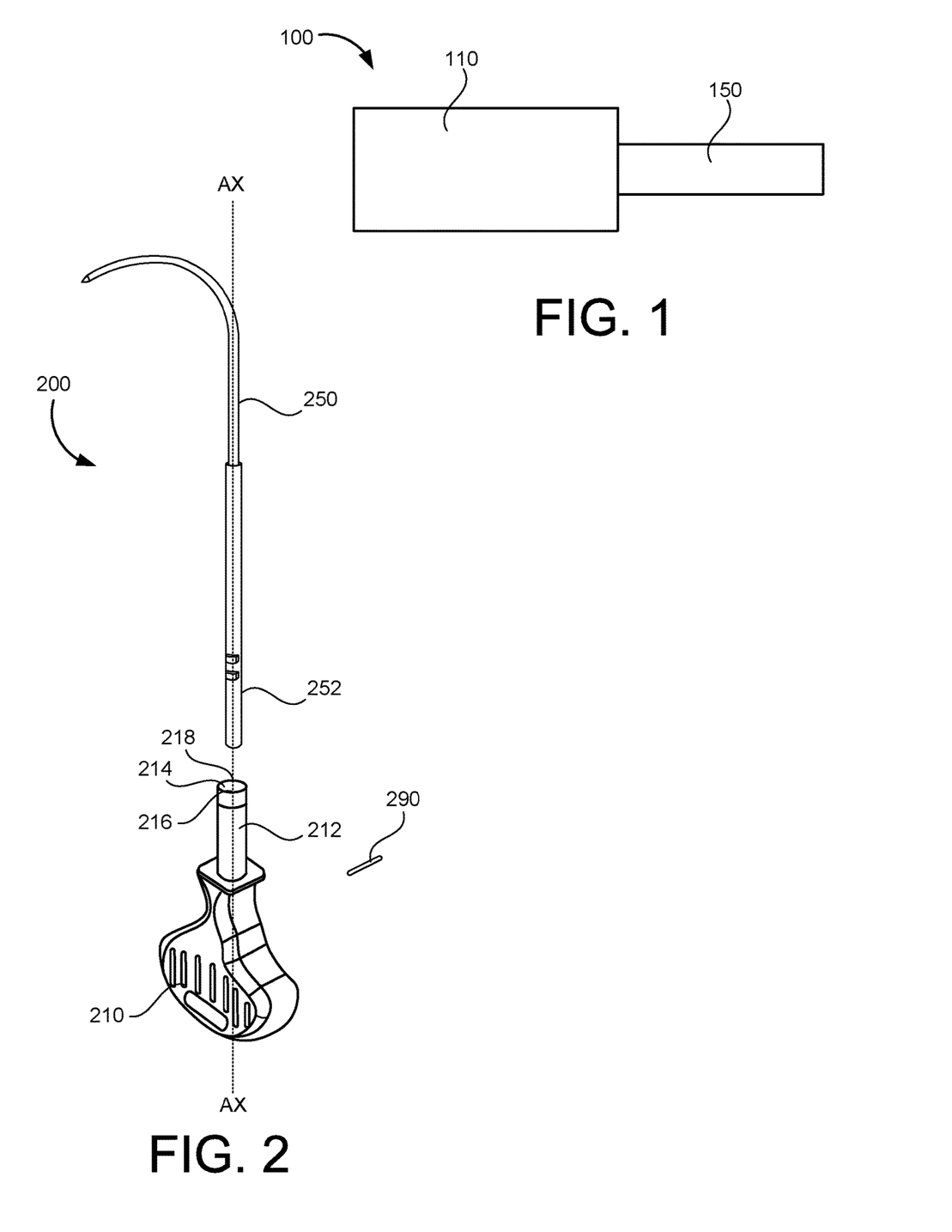
FIG. 1 is a schematic illustration of a medical device according to an embodiment.
FIG. 2 is an exploded view of a medical device according to an embodiment of the invention.
Figure 3:
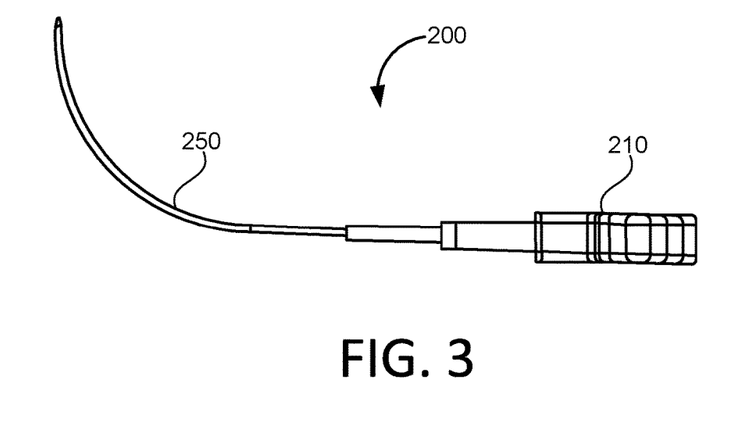
FIG. 3 is a side view of the medical device of FIG. 2.
Figure 4:
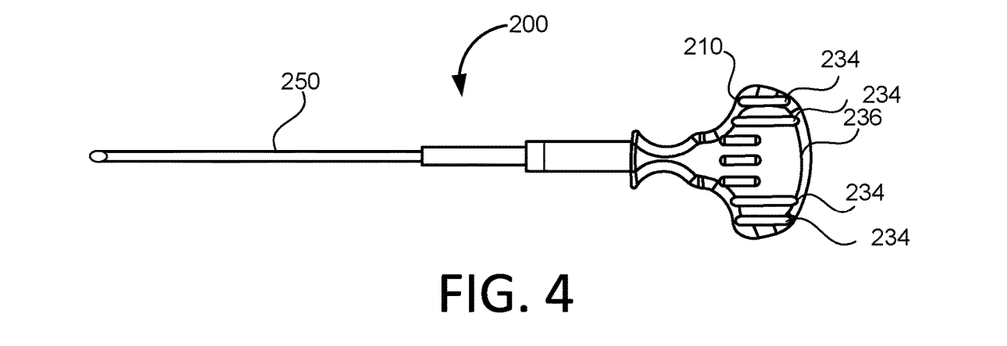
FIG. 4 is a top view of the medical device of FIG. 2.

FIG. 1 is a schematic illustration of a medical device 100 according to an embodiment of the invention. The medical device 100 may be used place or dispose an implant within a body of a patient. For example, the medical device 100 may be coupled to a bodily implant, inserted into a body of a patient, uncoupled from the bodily implant, and removed from the body of the patient leaving the implant disposed within the body of the patient. In some embodiments, the medical device 100 is configured to be used in a pelvic floor procedure. For example, the medical device 100 may be used to insert or implant a pelvic floor implant, such as a sling configured to provide support to a pelvic organ or portion of the body. In other embodiments, the medical device 100 is configured to be used in a different area of the body. For example, the medical device 100 may be used to place or dispose an implant in a location of the body other than the pelvic or abdominal region of the patient.

The medical device 100 includes a handle member 110 and a needle member 150. The handle member 110 is coupled to the needle member 150. In other words, the needle member 150 extends from the handle member 110. In some embodiments, the handle member 110 is fixedly coupled to the needle member 150. In such embodiments, the handle member 110 may not be removed or uncoupled from the needle member 150 without breaking the device 100. In other embodiments, the handle member 110 is removably coupled to the needle member 150. In yet other embodiments, the handle member 110 and the needle member 150 are monolithic or unitarily formed (formed of one piece of material).

In some embodiments, the medical device 100 is configured to be used in more than one medical procedure and is configured to be washed or cleaned and sterilized between uses. For example, in some embodiments, the medical device 100 is configured to be used in a first medical procedure on a first patient. Then the medical device 100 may be cleaned or washed and sterilized and used in a second medical procedure on a different patient. In some embodiments, the medical device 100 may be used in more than 2 different medical procedures. For example, in some embodiments, the medical device 100 is configured to be used in 10, 20 or more than 20 medical procedures (after being cleaned or washed and sterilized between each medical procedure).

In some embodiments, the medical device 100 is formed or made of materials that can be washed or cleaned and sterilized and reused in additional medical procedures. For example, in some embodiments, the needle member 150 is formed or made of a metal material, such as stainless steel. In some embodiments, the handle member 110 is formed or made of a polymer material that is configured to be washed or cleaned. For example, in some embodiments, the handle member is made of a polyphenylsulfone material. For example, the handle member 110 may be machined from polyphenylsulfone. In other embodiments, the handle member 110 may be made or fabricated from aluminum, stainless steel, or ultem (polyetherimide). In yet other embodiments, the handle member 110 may be made or fabricated from polyetherimide, polysulfone, polyethersulfone, stainless steel, or anodized aluminium.

The handle member 110 may be of any size or shape. In some embodiments, the handle member 110 is sized to fit in a hand of a physician. In some embodiment, the handle member 110 includes contours or features that facilitate the grasping of the device by the physician or the movement of the device into the body of the patient to aid in the advancement and placement of the device within the body of the patient.

The needle member 150 may be of any size or shape. In some embodiments, the needle member 150 is sized and shaped to be advanced and placed within the desired location within the body of the patient. In some embodiments, the needle member 150 includes a linear portion. In some embodiments, the needle member 150 includes a curved portion or portions. In some embodiments, the needle member 150 is linear (devoid of any curved portions).

FIGS. 2-16 illustrate a medical device 200 according to an embodiment of the invention. The medical device 200 may be used place or dispose an implant within a body of a patient. For example, the medical device 200 may be coupled to a bodily implant, inserted into a body of a patient, uncoupled from the bodily implant, and removed from the body of the patient leaving the implant disposed within the body of the patient. In some embodiments, the medical device 200 is configured to be used in a pelvic floor procedure. For example, the medical device 200 may be used to insert or implant a pelvic floor implant, such as a sling configured to provide support to a pelvic organ or portion of the body. In other embodiments, the medical device 200 is configured to be used in a different area of the body. For example, the medical device 200 may be used to place or dispose an implant in a location of the body other than the pelvic or abdominal region of the patient.

The medical device 200 includes a handle member 210 and a needle member 250. The handle member 210 is coupled to the needle member 250. In other words, the needle member 250 extends from the handle member 210. In the illustrated embodiment, the handle member 210 is fixedly coupled to the needle member 250. In such embodiments, the handle member 210 may not be removed or uncoupled from the needle member 250 without breaking the device 200.

In the illustrated embodiment, the handle member 210 includes an extension portion 212. The extension portion 212 defines an opening 214 and a cavity or lumen 216. Specifically, an internal or interior sidewall 218 of the handle member 210 defines the cavity or lumen 216. In the illustrated embodiment, a proximal portion 252 of the needle member 250 is disposed within the cavity or lumen 216. In some embodiments, the handle member 210 is coupled to the needle member 250 via a frictional fit between an outer surface of the needle member 250 and the internal sidewall 218 of the handle member 210. In some embodiments, an adhesive, such as a glue, an epoxy, or other adhesive, is used to couple the handle member 210 to the needle member 250. For example, the adhesive may be placed within the cavity or lumen 216 of the handle member 210 to couple the handle member 210 to the needle member 250. In some embodiments, the projection or projection portion 254 (as described below) defines a location for the adhesive to collect or pool to facilitate the coupling of the needle member 250 to the handle member 210.

In the illustrated embodiment, the needle member 250 defines a projection or projection portion 254 between a pair of grooves or slots 256. The projection portion 254 is configured be disposed within the cavity or lumen 216 when the needle member 250 is coupled to the handle member 210. The projection portion 254 is configured to engage the sidewall 218 to help facilitate the coupling of the needle member 250 to the handle member 210. For example, in some embodiments, the projection portion 254 provides a location for an adhesive to collect or pool to help couple the needle member 250 to the handle member 210. In some embodiments, the needle member 250 defines more than one projection or projection portion.

In the illustrated embodiment, the medical device 200 includes a pin 290. In some embodiments, the pin 290 is a spring pin. The pin 290 is configured to extend through an opening 220 defined by the handle member 210 and through an opening 255 defined by the needle member 250. As the pin 290 extends through a portion of each of the handle member 210 and the needle member 250, the pin 290 is configured to help couple the handle member 210 to the needle member 250. In some embodiments, the pin and/or the adhesive help prevent the needle member 250 from being removed from the handle member 210 and/or rotated with respect to the handle member 210. In some embodiments, the proximal portion 252 of the needle member 250 is inserted into the cavity or lumen 216 until the opening 220 is aligned with the opening 255. The pin 290 can then be inserted into the openings such that it extends through a portion of each of the handle member 210 and the needle member 250.

In other embodiments, the handle member 210 is removably coupled to the needle member 250. In yet other embodiments, the handle member 210 and the needle member 250 are monolithic or unitarily formed (formed of one piece of material).

The handle member 210 may be of any size or shape. In some embodiments, the handle member 210 is sized to fit in a hand of a physician. In some embodiment, the handle member 210 includes contours or features that facilitate the grasping of the device by the physician or the movement of the device into the body of the patient to aid in the advancement and placement of the device within the body of the patient.

Figure 5:
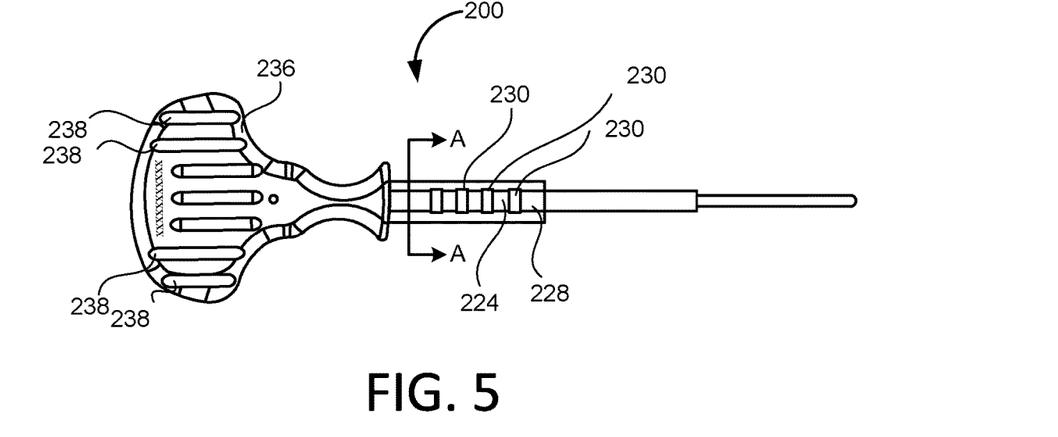
FIG. 5 is a bottom view of the medical device of FIG. 2.
Figure 6:
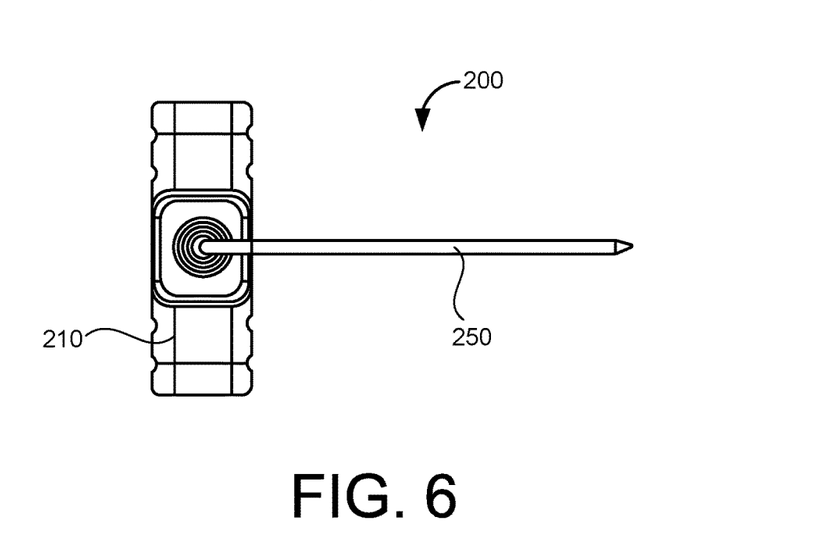
FIGS. 6 and 7 are end views of the medical device of FIG. 2.
Figure 7:
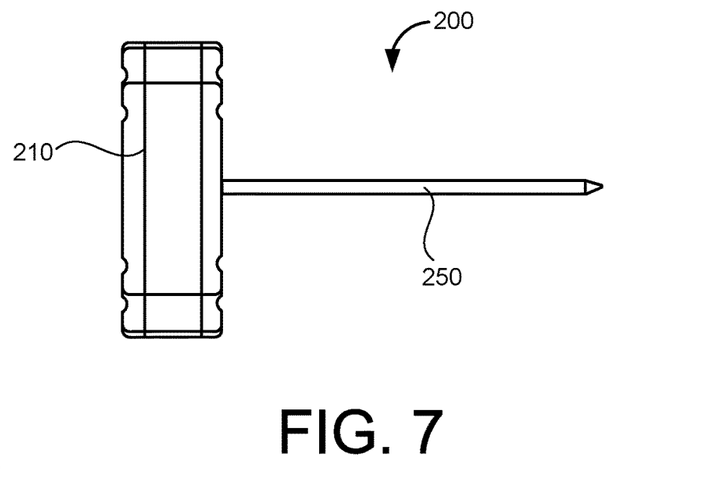
Figure 8:
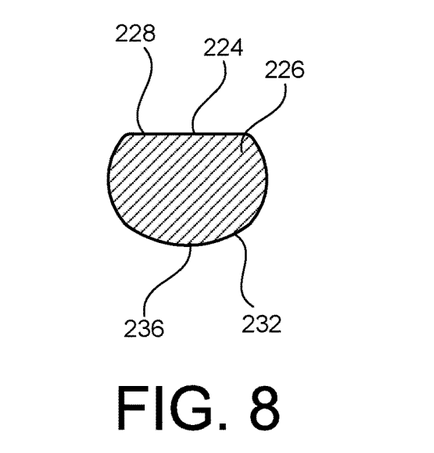
FIG. 8 is a cross-sectional view taken along line A-A of FIG. 5.

In the illustrated embodiment, the extension portion 212 of the handle member 210 includes a finger pad 224 that is configured to facilitate the control and movement of the medical device 200. In the illustrated embodiment, the finger pad 224 is on the bottom side 226 of the handle member 210 (the bottom side being the side in which the curved portion of the needle member 250 curves away from). The finger pad 224 includes a flat portion 228 and grooves or slots 230. As best illustrated in FIGS. 5 and 8, the extension portion 212 includes a rounded portion 232 (on the top side 236 of the handle member 210) and the flat or planar portion 228. In some embodiments, finger pad 224 includes a portion that is substantially flat or planar. In the illustrated embodiment, grooves or slots 230 extend substantially perpendicularly to an axis AX defined by the handle member 210 and the medical device 200. In other embodiments, the slots or grooves extend at a different angle with respect to the axis AX defined by the medical device 200. In the illustrated embodiment, the finger pad 224 includes four grooves or slots 230. In other embodiments, the finger pad 224 includes or defines more or less than four grooves or slots.

In some embodiments, a physician may place a finger or fingers on the finger pad 224 while the medical device 200 is in use. For example, a physician may place a finger or fingers on the finger pad 224 while the medical device 200 is disposed within or being moved into a body of a patient. The finger pad 224, including the substantially flat portion 228 and/or the grooves or slots 230 facilitate the grasping and/or control of the device 200 by the physician.

In the illustrated embodiment, the proximal portion 232 of the handle member 210 also includes or defines grooves or slots. Grooves or slots 234 are disposed on the bottom side 226 of the handle member 210. Grooves or slots 238 are disposed on the top side 236 (which is disposed opposite the bottom side 226) of the handle member 210. In some embodiments, the grooves or slots 234 and the grooves or slots 238 are configured to facilitate the grasping or control of the device 200 by the physician. In the illustrated embodiment, the grooves or slots 234 and the grooves or slots 238 extend substantially parallel to the longitudinal axis AX of the medical device 200.

The needle member 250 may be of any size or shape. In some embodiments, the needle member 250 is sized and shaped to be advanced and placed within the desired location within the body of the patient. In some embodiments, the needle member 250 is between 11 and 13 inches long. In other embodiments, the needle member is shorter than 11 inches. In yet other embodiments, the needle member 250 is longer than 13 inches.

Figure 15:
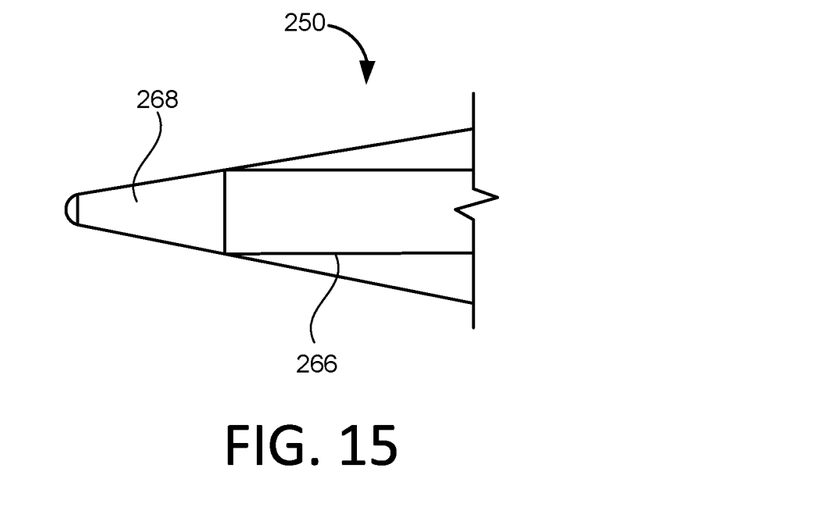
FIG. 15 is a side view of a portion of the needle member of the medical device of FIG. 2.

In the illustrated embodiment, the needle member includes a linear portion 262 and a curved portion 264. In other embodiments, the needle member 250 is linear (devoid of a curved portion). In the illustrated embodiment, as best illustrated in FIG. 15, the distal portion 266 of the needle member 250 includes a sharp tip 268. The sharp tip 268 is configured to cut or pierce bodily tissue as the device 200 is placed or moved within a body of a patient.

Figure 9:
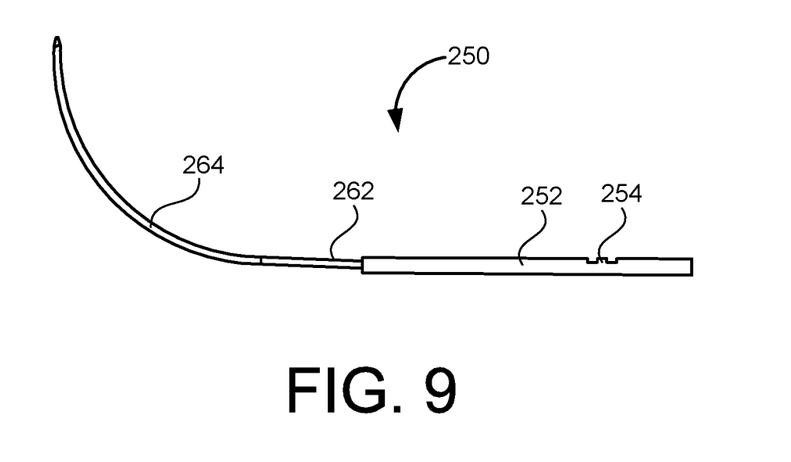
FIG. 9 is a side view of the needle member of the medical device of FIG. 2.
Figure 10:
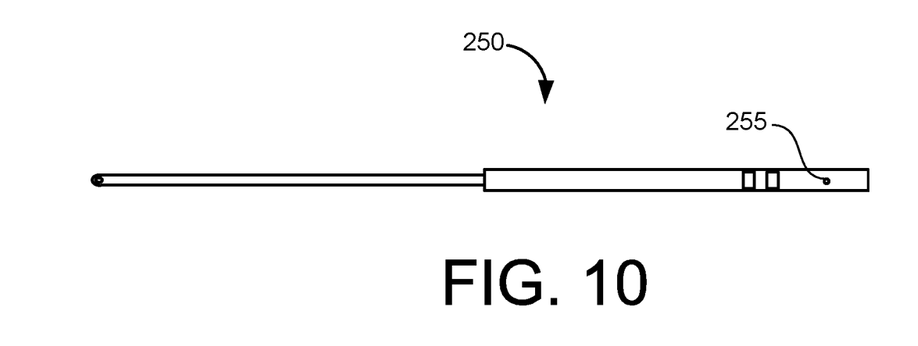
FIG. 10 is a top view of the needle member of the medical device of FIG. 2.
Figure 11:
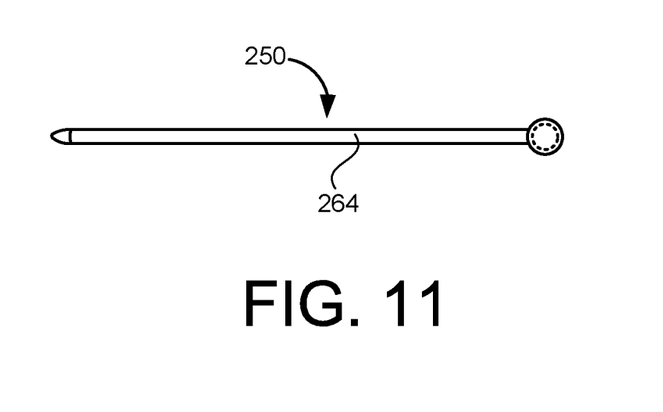
FIG. 11 is an end view of the needle member of the medical device of FIG. 2.
Figure 12:
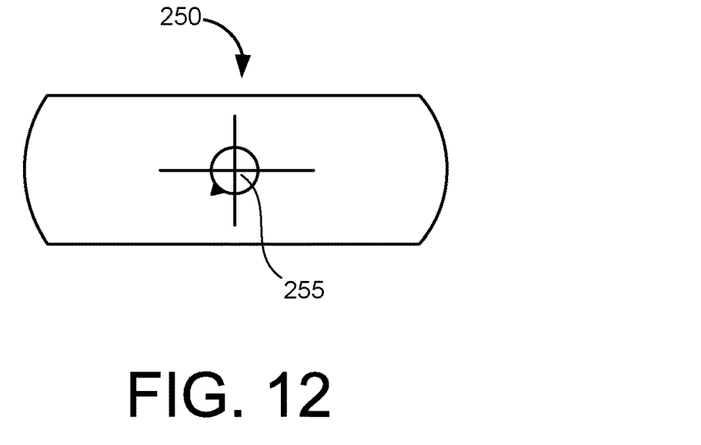
FIG. 12 is a top view of a portion of the needle member of the medical device of FIG. 2.
Figure 13:
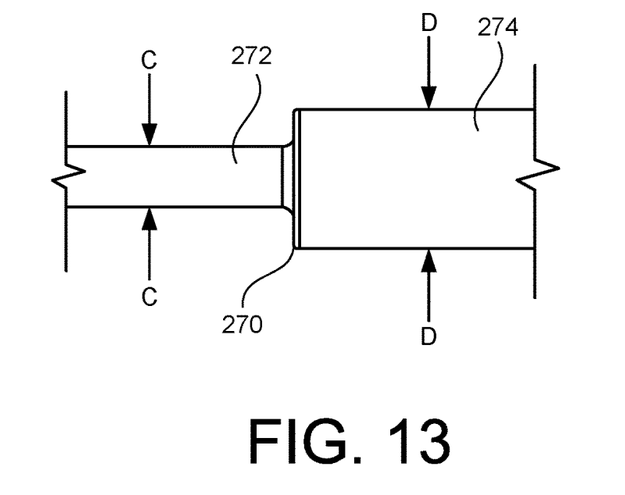
FIG. 13 is a top view of a portion of the needle member of the medical device of FIG. 2.
Figure 14:
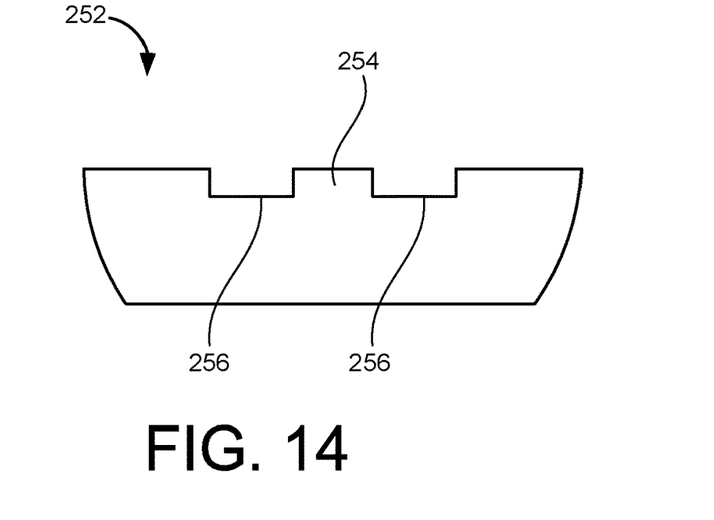
FIG. 14 is a side view of a portion of the needle member of the medical device of FIG. 2.

The needle member 250 also includes or defines a shoulder or ridge member 270. As best illustrated in FIGS. 9 and 13, the shoulder or ridge member 270 is located between a narrow or thin portion 272 of the needle member 250 and a wide or thicker portion 274 of the needle member 250. In some embodiments, the needle member 250 is tubular or has a circular cross section and the thin portion 272 has a size or diameter C that is smaller than the size or diameter D of the thick portion 274.

Figure 16:
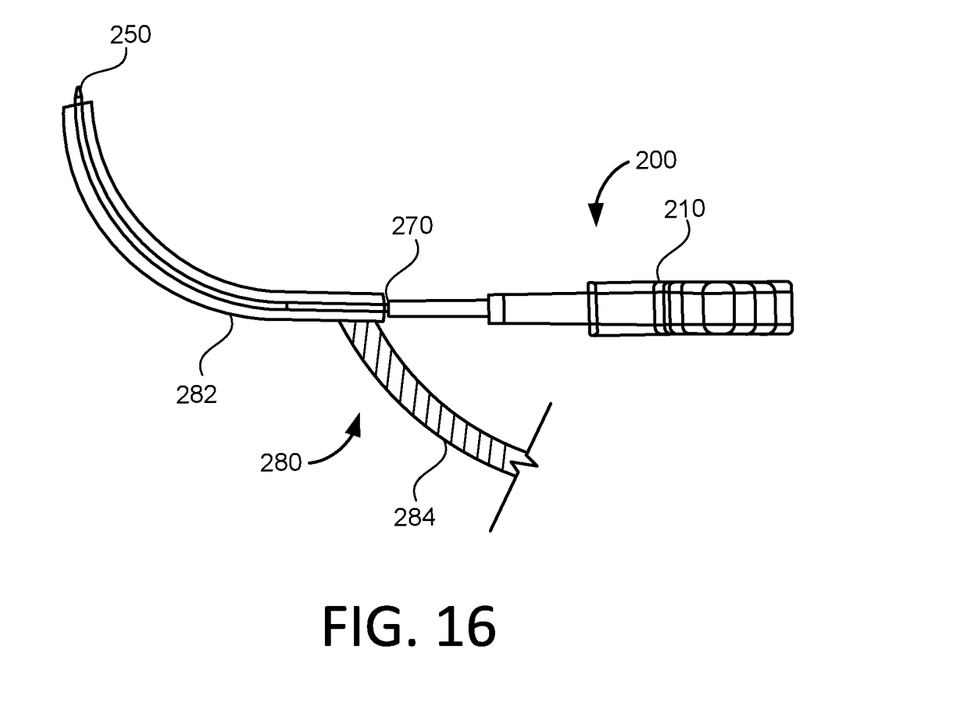
FIG. 16 is a side view of the medical device of FIG. 2 coupled to an implant.

The shoulder or ridge member 270 is configured to engage or contact a bodily implant when the bodily implant is coupled to the needle member 250. As best illustrated in FIG. 16, the needle member 250 may be coupled to a bodily implant 280. In the illustrated embodiment, the bodily implant includes a tubular member (such as a dilator) 282 and a mesh portion 284. In the illustrated embodiment, the tubular member 282 may be slid or moved over the thin portion 272 of the needle member 250 until the tubular member 282 contacts or engages the shoulder or ridge member 270. The shoulder or ridge 270 is configured to contact the tubular member 282 such that the tubular member 282 stays in place on the needle member 250 and does not continue to slide or move down the needle member 250 as the device 200 and the implant 280 are moved or pushed into a body of a patient. Once the implant 280 is in the correct place within the body of the patient, the device 200 may be removed from the body and the tubular member 282 of the implant 280 will slide off of the needle member 250 and remain in place within the body of the patient.

In some embodiments, the medical device 200 is configured to be used in more than one medical procedure and is configured to be washed or cleaned and sterilized between uses. For example, in some embodiments, the medical device 200 is configured to be used in a first medical procedure on a first patient. Then the medical device 200 may be cleaned or washed and used in a second medical procedure on a different patient. In some embodiments, the medical device 200 may be used in more than 2 different medical procedures. For example, in some embodiments, the medical device 200 is configured to be used in 10, 20 or more than 20 medical procedures (after being cleaned or washed between each medical procedure).

In some embodiments, the medical device 200 is formed or made of materials that can be washed or cleaned and sterilized and reused in additional medical procedures. For example, in some embodiments, the needle member 250 is formed or made of a metal material, such as stainless steel. In some embodiments, the handle member 210 is formed or made of a polymer material that is configured to be washed or cleaned. For example, in some embodiments, the handle member is made of a polyphenylsulfone material. For example, the handle member 210 may be machined from polyphenylsulfone.

Figure 17:
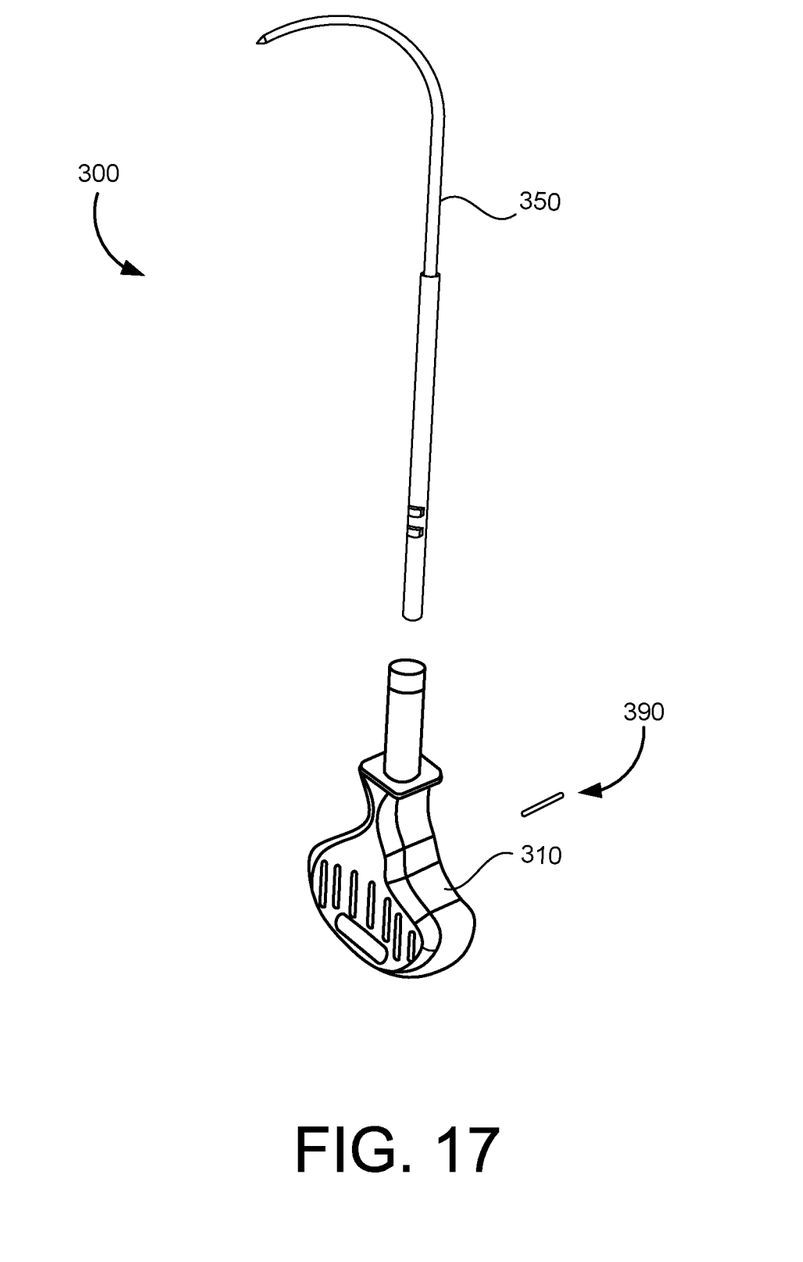
FIG. 17 is an exploded view of another embodiment of a medical device according to an embodiment.

FIG. 17 is an exploded view of a medical device 300 according to another embodiment of the invention. The medical device includes a handle member 310, a needle member 350, and a pin 390. As discussed above, the needle member 350 may be of any size or shape. In the illustrated embodiment, the needle member 350 has a curved portion that is larger or more curved. The curved portion of the needle member 350 may be of any radius. The radius of curvature may be chosen for the location of the body in which the device 300 will be placed. For example, in some embodiments, the radius of curvature is between 3 and 4 inches. In other embodiments, the radius of curvature is less than 3 inches or greater than 4 inches.

Figure 18:
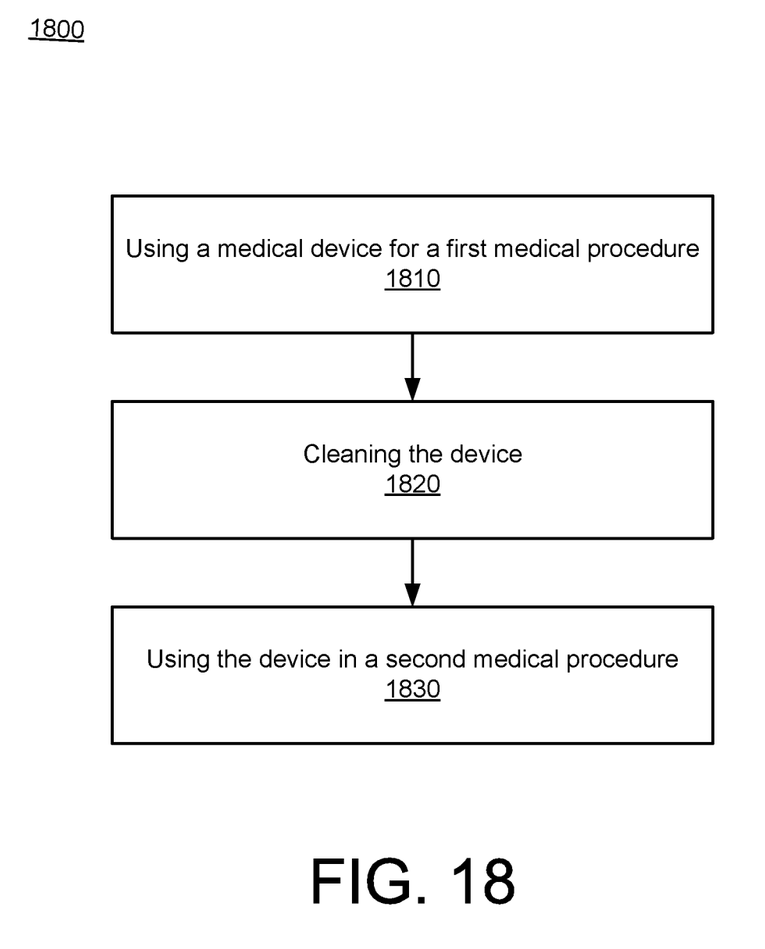
FIG. 18 is a flow chart of a method according to an embodiment.

FIG. 18 is a flow chart of a method 1800 according to an embodiment of the invention. At 1810, a medical device, such as medical device 100, medical device 200, or medical device 300 may be used for a first medical procedure. For example, the device may be used to place a bodily implant within a body of a first patient. In some embodiments, the device may be used to place a bodily implant within a pelvic region of a patient. In other embodiments, the device may be used in a medical procedure at a different location of a body of a patient.

At 1820, the medical device may be cleaned or washed. For example, conventional or known methods may be used to clean, wash, and sterilize the medical device. For example, in some embodiments, the medical device may be cleaned using a manual method (such as by using a brush or other cleaning tool), a mechanical method (such as a cleaning machine), or a sterilization method or autoclave method (such as temperature or steam sterilization). In some embodiments, cleaning may be done using water and a detergent and manually brushing the device to clean it. Additionally, in some embodiments, sterilization methods can include steam sterilization, or the use of ethylene oxide and hydrogen peroxide. At 1830, the medical device may be used in a second medical procedure. For example, the device may be used in a medical procedure on a second patient different than the first patient.

According to an aspect, a medical device includes a needle member and a handle member. The handle member is coupled to the needle member. The handle member has a substantially flat portion. The handle member defines a groove. The groove is disposed on the substantially flat portion of the handle member.

In some aspects, the handle member defines a longitudinal axis and the groove extends in a direction substantially perpendicular to the longitudinal axis of the handle member. In some aspects, the handle member has a rounded portion, the rounded portion is disposed on a top side of the handle member, the substantially flat portion is disposed on a bottom side of the handle member, the top side of the handle member is opposite the bottom side of the handle member.

In some aspects, the needle member includes a curved portion. In some aspects, the needle member includes a substantially linear portion and a curved portion. In some aspects, the needle member includes a first portion having a first diameter and a second portion having a second diameter, the second diameter is larger than a first diameter. In some aspects, the needle member defines a ridge configured to contact a portion of a bodily implant.

In some aspects, the handle member is coupled to the needle member via an adhesive. In some aspects, the handle member defines a cavity, at least a portion of the needle member is disposed within the cavity. In some aspects, the handle member defines a cavity having an inner surface, at least a portion of the needle member is disposed within the cavity, the needle portion having a projection, the projection is configured to be disposed within the cavity and being configured to engage the inner surface of the cavity of the handle member.

In some aspects, the needle member is formed of a metal material. In some aspects, the handle member is formed of a plastic-based material. In some aspects, the medical device is configured to be cleaned and/or sterilized after use.

In some aspects, a medical device includes a needle member and a handle member. The needle member defines a projection. The handle member is coupled to the needle member. The handle member defines a cavity having an inner surface. The handle member is coupled to the needle member such that the projection defined by the needle member is disposed within the cavity and engages the inner surface of the cavity.

In some aspects, the needle member includes a curved portion. In some aspects, the needle member includes a substantially linear portion and a curved portion. In some aspects, the needle member includes a first portion having a first diameter and a second portion having a second diameter, the second diameter being larger than a first diameter. In some aspects, the needle member defines a ridge configured to contact a portion of a bodily implant. In some aspects, the handle member is coupled to the needle member via an adhesive.

In some aspects, a method includes using a device for a first medical procedure, the medical device having a needle member, and a handle member coupled to the needle member, the handle member having a substantially flat portion, the handle member defining a groove, the groove being disposed on the substantially flat portion; cleaning the device; and using the medical device for a second medical procedure.

In some aspects, the use or the device for the first medical procedure includes placing a bodily implant within a body of a patient. In some aspects, the handle member of the device defines a longitudinal axis, the groove extends in a direction substantially perpendicular to the longitudinal axis of the handle member. In some aspects, the handle member of the device has a rounded portion, the rounded portion being disposed on a top side of the handle member, the substantially flat portion being disposed on a bottom side of the handle member, the top side of the handle member being opposite the bottom side of the handle member.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device comprising:
   a needle member including a ridge disposed between a first portion having a first diameter and a second portion having a second diameter, the second diameter being smaller than the first diameter, the ridge being configured to engage an implant having a tubular member and a mesh, the needle member including a first end and a second end portion opposite the first end, the first end having a tip configured to pierce bodily tissue, the second end having a circular cross-section;
   a handle member including an extension portion extending from the handle member, the extension portion includes a flat portion being disposed on a first side of the handle member and a curved portion being disposed on a second side, opposite the first side, of the handle member, the flat portion defines a groove that extends in a direction substantially perpendicular to a longitudinal axis of the handle member, the first portion of the needle member being configured to be removably coupled to the handle member; and
   a pin configured to be inserted in an opening in the handle member and an opening in the needle member, such that the pin extends through at least a portion of the needle member and at least a portion of the handle member, the pin being configured to prevent rotation of the needle member with respect to the handle member.

2. The medical device of claim 1, wherein the handle member has a rounded portion and a substantially flat portion, the rounded portion being disposed on a top side of the handle member, the substantially flat portion being disposed on a bottom side of the handle member, the top side of the handle member being opposite the bottom side of the handle member.

3. The medical device of claim 1, wherein the needle member includes a substantially linear portion and a curved portion.

4. The medical device of claim 1, wherein the handle member is coupled to the needle member via an adhesive.

5. The medical device of claim 1, wherein the handle member defines a cavity, at least a portion of the needle member being disposed within the cavity.

6. The medical device of claim 1, wherein the handle member defines a cavity having an inner surface, at least a portion of the needle member being disposed within the cavity, the at least a portion of the needle member having a projection, the projection being configured to be disposed within the cavity and being configured to engage the inner surface of the cavity of the handle member.

7. The medical device of claim 1, wherein:
   the opening in the handle member is arranged along a longitudinal axis that is orthogonal to the longitudinal axis of the handle member; and
   the opening in the needle is arranged along a longitudinal axis that is orthogonal to a longitudinal axis of the needle.

8. The medical device of claim 1, wherein the first portion of the needle member includes a projection member that is configured to engage with a portion of the extension member.

9. The medical device of claim 1, wherein the groove is a first groove, the handle member defines a second groove, the second groove extending in a direction substantially parallel to the longitudinal axis of the handle member.

10. The medical device of claim 1, wherein the flat portion of the handle member is fixedly coupled to the curved portion of the handle member.

11. The medical device of claim 1, wherein the handle member is machined from a piece of material.

12. A medical device comprising:
   a needle member having a proximal end portion and a distal end portion, the proximal end portion defining a longitudinal axis, the needle includes a ridge disposed between a first portion having a first diameter and a second portion having a second diameter, the second diameter being different than the first diameter, the ridge being configured to engage an implant having a tubular member and a mesh, the needle member, at the proximal end portion, including a first groove and a second groove and a projection disposed between the first groove and the second groove, the projection extends in a direction substantially perpendicular to the longitudinal axis of the needle member;

a handle member coupled to the needle member, the handle member defining a cavity having an inner surface, the handle member being coupled to the needle member such that the projection defined by the needle member is disposed within the cavity, the handle member including a flat portion that defines a first groove that extends in a direction substantially perpendicular to a longitudinal axis of the handle member, the handle member defining a second groove, the second groove of the handle member extending in a direction substantially parallel to the longitudinal axis of the handle member; and a pin configured to be inserted in an opening in the handle member and an opening in the needle member, such that the pin extends through at least a portion of the needle member and at least a portion of the handle member, the pin being configured to prevent rotation of the needle member with respect to the handle member, the first groove of the needle member and the second groove of the needle member being configured to facilitate coupling the needle member to the handle member.

13. The medical device of claim 12, wherein the needle member includes a curved portion.

14. The medical device of claim 12, wherein the needle member includes a substantially linear portion and a curved portion.

15. The medical device of claim 12, wherein the second diameter of the second portion of the needle member is smaller than a first diameter of the first portion of the needle member.

16. The medical device of claim 12, wherein the handle member is coupled to the needle member via an adhesive.

17. The medical device of claim 12, wherein:
the opening in the handle member is arranged along a longitudinal axis that is orthogonal to a longitudinal axis of the handle member; and
the opening in the needle is arranged along a longitudinal axis that is orthogonal to the longitudinal axis of the needle.

18. The medical device of claim 11, wherein the needle member includes a proximal end having a circular cross-section.

* * * * *